US011534218B2

(12) United States Patent
Daly et al.

(10) Patent No.: US 11,534,218 B2
(45) Date of Patent: *Dec. 27, 2022

(54) ORTHOPEDIC BREAK-OFF SCREWS, TOOLS FOR INSERTING SUCH SCREWS, AND RELATED SYSTEMS AND METHODS

(71) Applicant: DePuy Synthes Products, Inc., Raynham, MA (US)

(72) Inventors: Anthony Daly, Coatesville, PA (US); Scott Lavoritano, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 132 days.

This patent is subject to a terminal disclaimer.

(21) Appl. No.: 16/695,779

(22) Filed: Nov. 26, 2019

(65) Prior Publication Data
US 2020/0093526 A1    Mar. 26, 2020

Related U.S. Application Data

(62) Division of application No. 15/370,409, filed on Dec. 6, 2016, now Pat. No. 10,531,903.

(51) Int. Cl.
*A61B 17/86* (2006.01)
*A61B 17/88* (2006.01)
*A61B 90/00* (2016.01)

(52) U.S. Cl.
CPC ........ *A61B 17/8605* (2013.01); *A61B 17/862* (2013.01); *A61B 17/8685* (2013.01);
(Continued)

(58) Field of Classification Search
CPC . A61B 17/86; A61B 17/8605; A61B 17/8685; A61B 17/88; A61B 17/8875
See application file for complete search history.

(56) References Cited

U.S. PATENT DOCUMENTS 10,531,903 B2 * 1/2020 Daly ................. A61B 17/8605
2004/0243139 A1   12/2004 Lewis et al.
(Continued)

FOREIGN PATENT DOCUMENTS

CN        103596511 A    2/2014
EP          0857465 A1   8/1998
(Continued)

*Primary Examiner* — Christopher J Beccia
(74) *Attorney, Agent, or Firm* — BakerHostetler

(57) ABSTRACT

A system for inserting an anchor member into bone includes a receiving member and an anchor member receivable within the receiving member. The receiving member is elongate along a longitudinal axis and has a proximal end and a distal end spaced from the proximal end along the longitudinal axis. The receiving member has an internal surface that defines a transmission element. The anchor member includes an engagement element configured to rotatably engage the transmission element such that the transmission element is configured to drive the anchor member in a distal direction relative to the transmission element so as to rotatably decouple the engagement element from the transmission element. The distal direction extends from the proximal end to the distal end of the receiving member and is parallel with the longitudinal axis.

20 Claims, 8 Drawing Sheets

(52) U.S. Cl.
 CPC ...... *A61B 17/8875* (2013.01); *A61B 17/8886* (2013.01); *A61B 17/8883* (2013.01); *A61B 2090/036* (2016.02); *A61B 2090/037* (2016.02)

(56) References Cited

U.S. PATENT DOCUMENTS

| | | | |
|---|---|---|---|
| 2005/0131408 | A1 | 6/2005 | Sicvol et al. |
| 2007/0005077 | A1 | 1/2007 | Null et al. |
| 2007/0218750 | A1* | 9/2007 | Corrao ............... A61B 17/8605 439/404 |
| 2007/0227314 | A1 | 10/2007 | Erickson et al. |
| 2008/0041196 | A1 | 2/2008 | Companioni et al. |
| 2009/0149889 | A1* | 6/2009 | Peterson .............. A61B 17/862 606/305 |
| 2010/0217333 | A1* | 8/2010 | McShane ........... A61B 17/8883 606/305 |
| 2013/0116694 | A1 | 5/2013 | Zurschmiede |
| 2014/0142715 | A1* | 5/2014 | McCormick ......... A61B 17/862 623/21.19 |
| 2014/0236247 | A1 | 8/2014 | Rezach |
| 2016/0262818 | A1 | 9/2016 | Granger et al. |

FOREIGN PATENT DOCUMENTS

| | | |
|---|---|---|
| JP | 2001-524392 A | 12/2001 |
| JP | 2007-513744 A | 5/2007 |
| JP | 2016-527062 A | 9/2016 |
| WO | 99/27261 | 6/1999 |
| WO | 2010/075505 A1 | 7/2010 |
| WO | 2015/054001 | 4/2015 |

\* cited by examiner

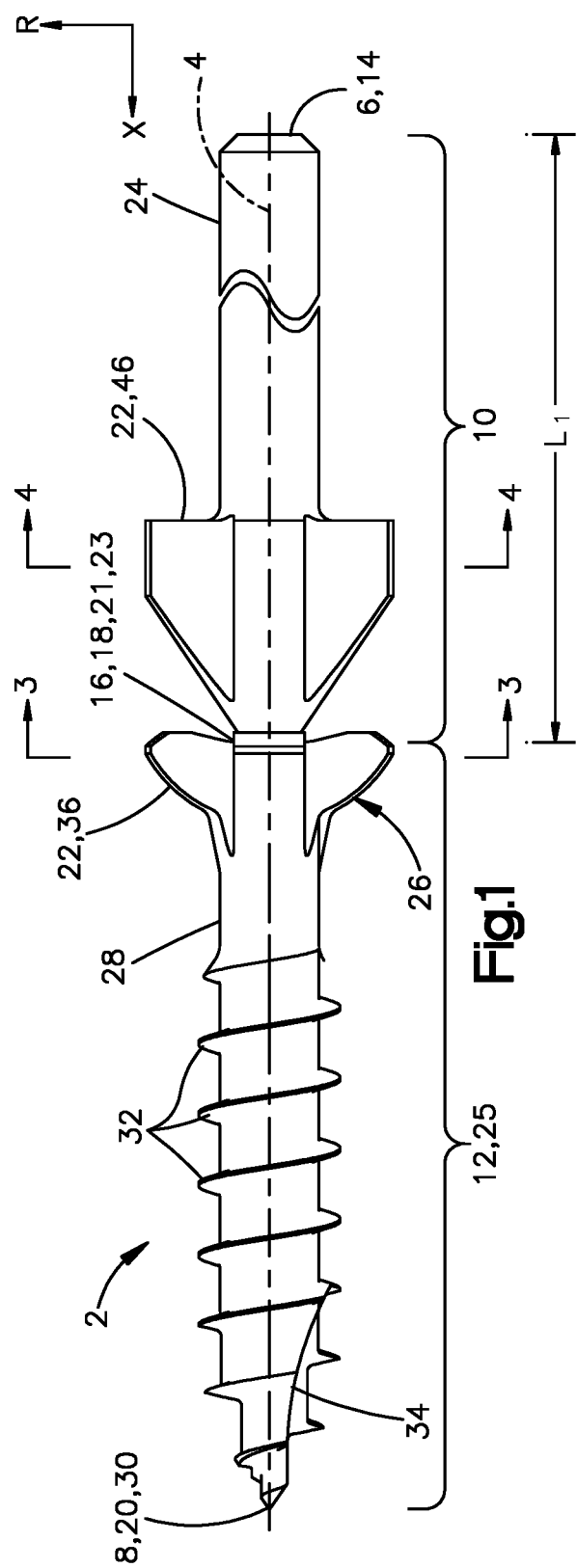
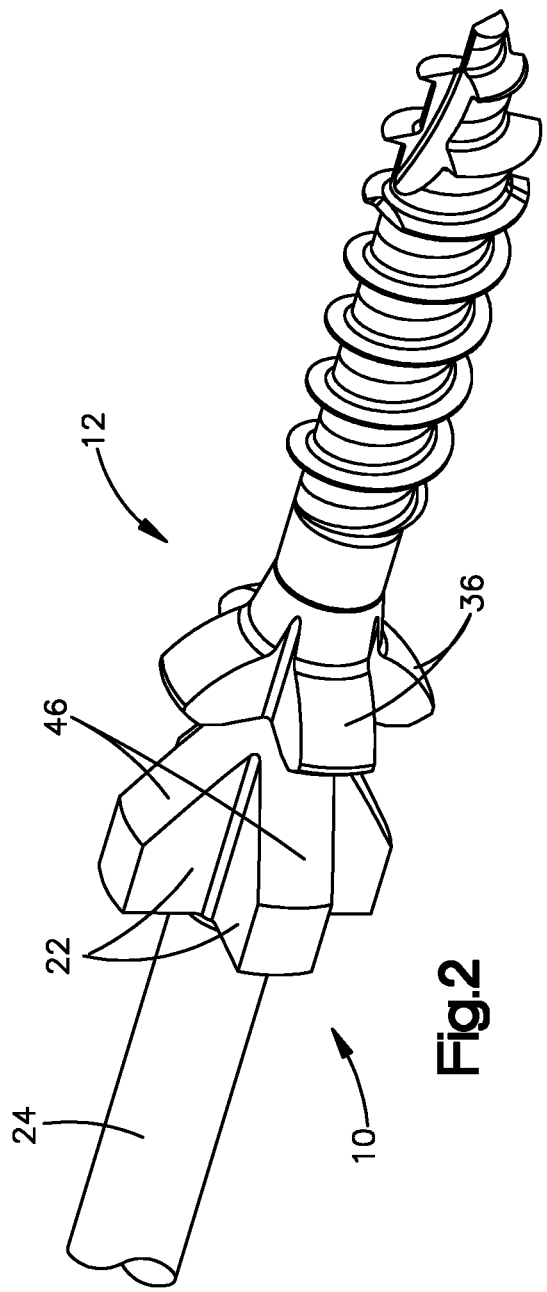

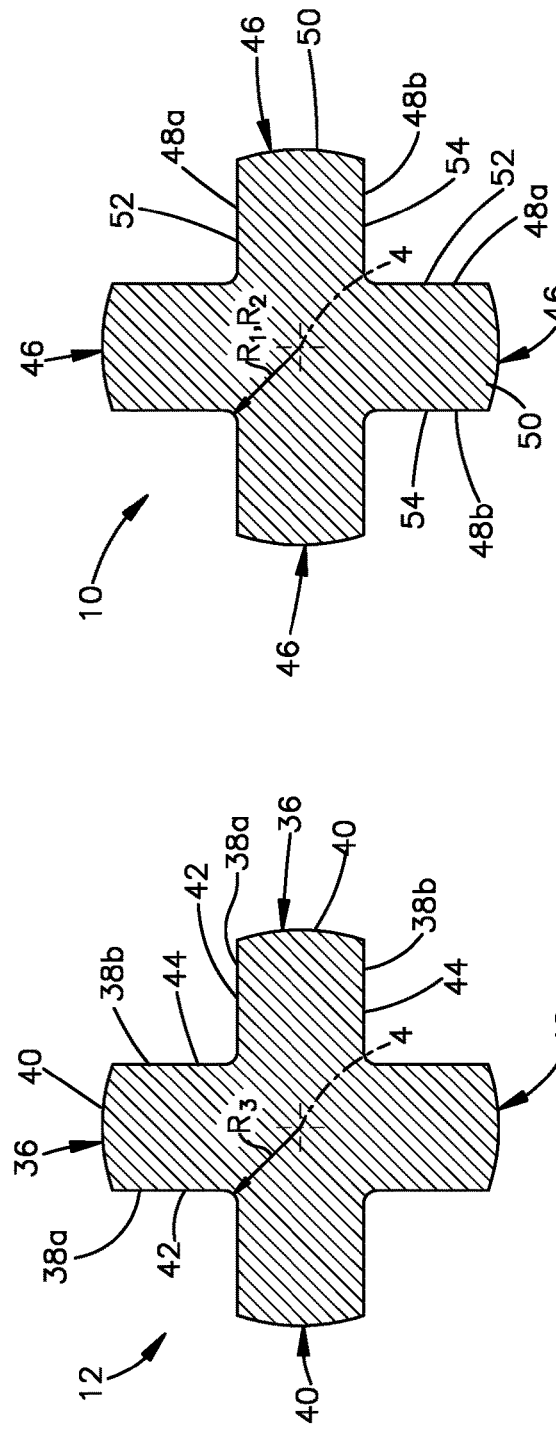
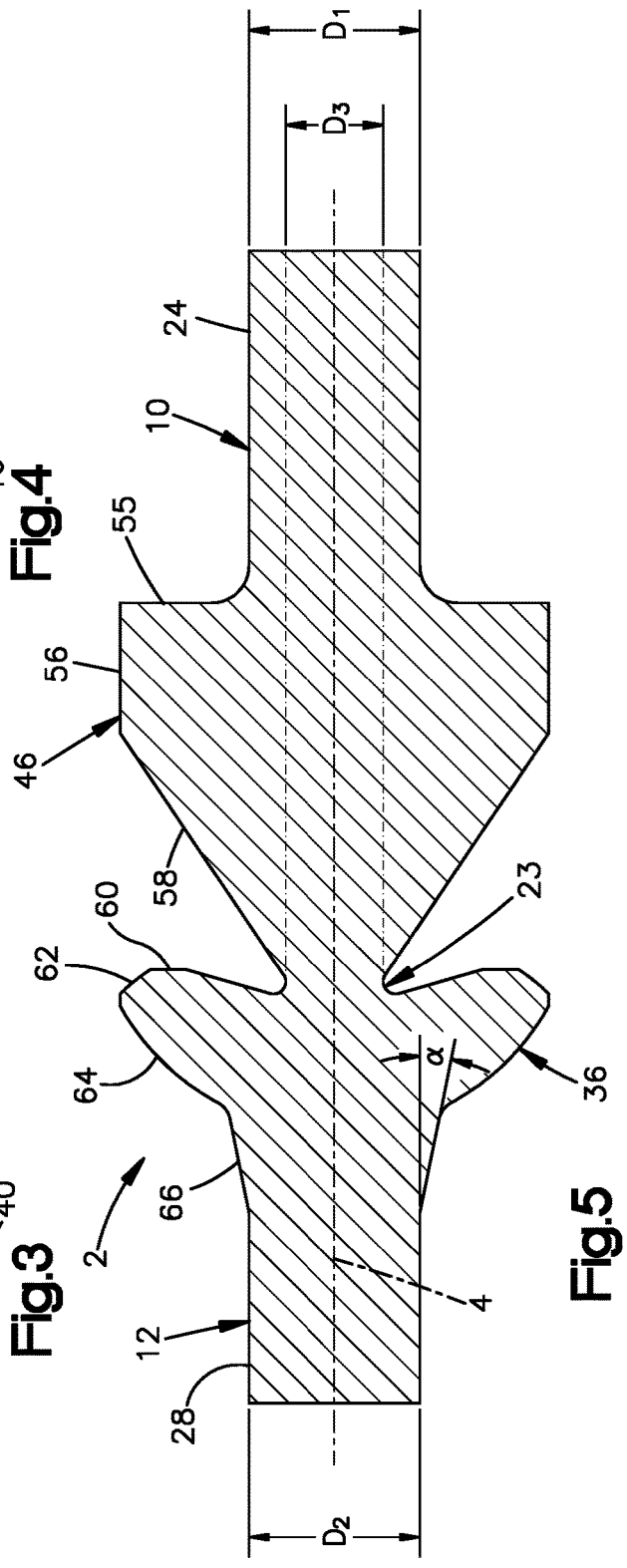

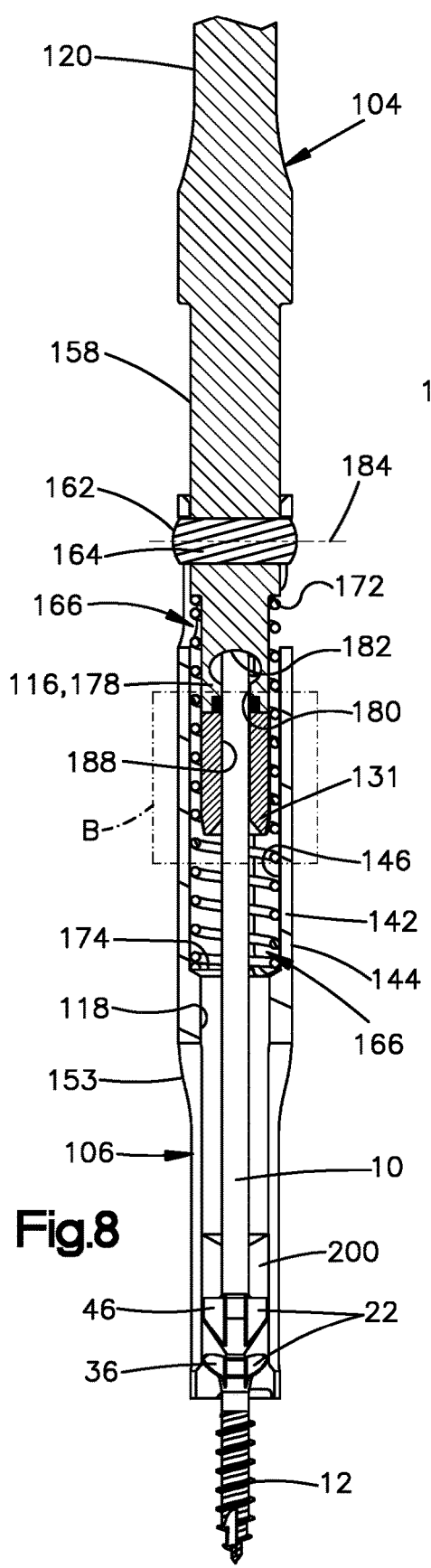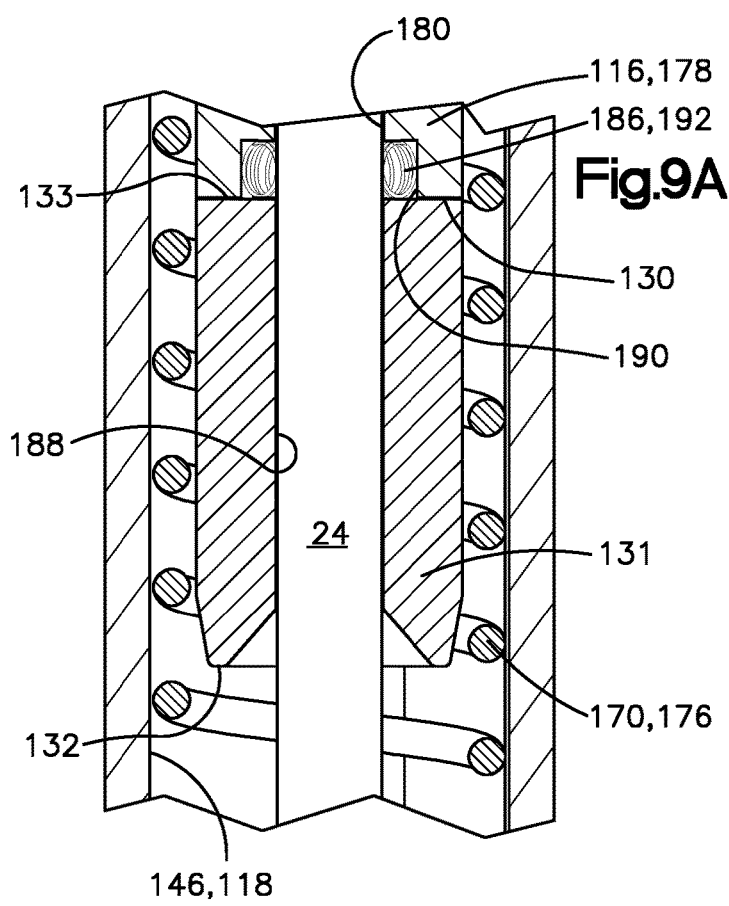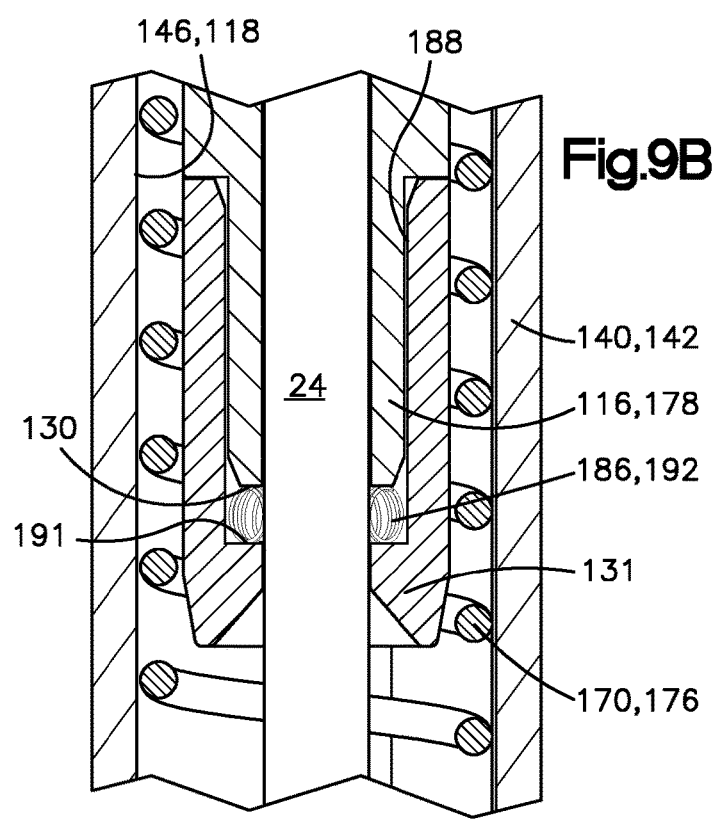

ORTHOPEDIC BREAK-OFF SCREWS, TOOLS FOR INSERTING SUCH SCREWS, AND RELATED SYSTEMS AND METHODS

CROSS REFERENCE TO RELATED APPLICATIONS

This application is a division of U.S. application Ser. No. 15/370,409 filed Dec. 6, 2016, the entire contents of which are hereby incorporated by reference.

FIELD OF THE DISCLOSURE

The present disclosure generally relates to bone fixation, and in particular relates to a bone fixation element with depth control features.

BACKGROUND

Bone fixation members, including bone screws, are conventionally utilized to correct a number of conditions or injuries involving the "lesser ray" bones of the hands and feet. By way of one non-limiting example, bone screws may be utilized in hallus valgus correction procedures of the foot, such as an osteotomy to correct a deformity of one or more of the hallus valgus angle (HVA) and the intermetatarsal angle (IMA), and/or an interphalangeal deformity. In particular, following the osteotomy, one or more bone screws may be utilized to affix osteotomized bone segments together. With bones sizes on the order of the smaller rays of the hands and feet, precise depth control and torque control of the associated bone screws may prevent damage caused to the bone segments in which the screws are inserted. However, precise depth and torque control is beneficial for bone screws designed for insertion in other bones as well, including so-called long bones, such as femurs, tibias, fibulas, humeri, radii, ulnas, metacarpals, metatarsals, and phalanges, and the like.

SUMMARY

In accordance with one embodiment, a system for inserting an anchor member into bone includes a receiving member and an anchor member receivable within the receiving member. The receiving member is elongate along a longitudinal axis and has a proximal end and a distal end spaced from the proximal end along the longitudinal axis. The receiving member has an internal surface that defines a transmission element. The anchor member includes an engagement element configured to rotatably engage the transmission element such that the transmission element is configured to drive the anchor member in a distal direction relative to the transmission element so as to rotatably decouple the engagement element from the transmission element. The distal direction extends from the proximal end to the distal end of the receiving member and is parallel with the longitudinal axis.

In accordance with an additional embodiment, a tool for driving an anchor member into bone during each of a first mode of operation and a second mode of operation includes a driver and a receiving member that has a proximal end and a distal end spaced from the proximal end along a longitudinal axis. The driver is attachable to the proximal end of the receiving member so at to rotate the receiving member about the longitudinal axis. The receiving member includes at least one torque transmission element. In the first mode of operation, the at least one torque transmission element is configured to engage at least one first engagement element and at least one second engagement element of a bone fixation element in a manner to rotate the anchor member about the longitudinal axis. In the second mode of operation, the at least one torque transmission element is configured to be decoupled from the at least one first engagement element and remain coupled to the at least one second engagement element. The tool includes a coupler coupled to each of the driver and the receiving member such that, during a first portion of the first mode of operation, the driver and the receiving member are translatably fixed relative to one another along the longitudinal axis, and, during a second portion of the first mode of operation, the driver and the receiving member are translatable relative to one another along the longitudinal axis.

In accordance with a further embodiment, a fixation element includes an anchor member having a proximal end and a distal end spaced from the proximal end along a central axis. The anchor member has a first plurality of engagement elements sized and configured to receive a driving torque that drives the anchor member. The fixation element includes a removable member having a proximal end and a distal end that is spaced from the proximal end of the removable member along the central axis. The removable member is adjoined with the anchor member at an interface, and the removable member includes a second plurality of engagement elements sized and configured to receive the driving torque. The interface is configured to fracture responsive to a predetermined torque differential between the removable member and the anchor member. The first plurality of engagement elements comprises a first plurality of projections. The second plurality of engagement elements comprises a second plurality of projections. Each of the projections of the first and second plurality of projections extends radially outward and defines a pair of opposed surfaces and a peripheral surface extending between the pair of opposed surfaces. The opposed surfaces of each pair are substantially parallel with one another and with the central axis.

DESCRIPTION OF THE DRAWINGS

The foregoing summary, as well as the following detailed description of preferred embodiments of the application, will be better understood when read in conjunction with the appended drawings. For the purposes of illustrating the embodiments of the present application, there is shown in the drawings certain embodiments. It should be understood, however, that the application is not limited to the precise arrangements and instrumentalities shown. In the drawings:

FIG. 1 is a side view of a fixation element for insertion into a bone, according to an embodiment of the present disclosure;

FIG. 2 is a perspective view of the fixation element of FIG. 1;

FIG. 3 is a sectional end view of an anchor member of the fixation element of FIG. 1, taken along section line 3-3 of FIG. 1;

FIG. 4 is sectional end view of a removable member of the fixation element of FIG. 1, taken along section line 4-4 of FIG. 1;

FIG. 5 is a magnified sectional view of an attachment location between an anchor member and a removable member of the fixation element of FIG. 1, taken along a longitudinal axis of the fixation element;

FIG. 8 is a sectional view of the driving tool of FIG. 6, taken along a longitudinal axis of the driving tool;

FIG. 9A is a magnified sectional view of a portion of the driving tool, as shown by dashed rectangle B in FIG. 8;

FIG. 9B is a magnified sectional view of a portion of the driving tool according to another embodiment of the present disclosure;

DETAILED DESCRIPTION

Figure 6:
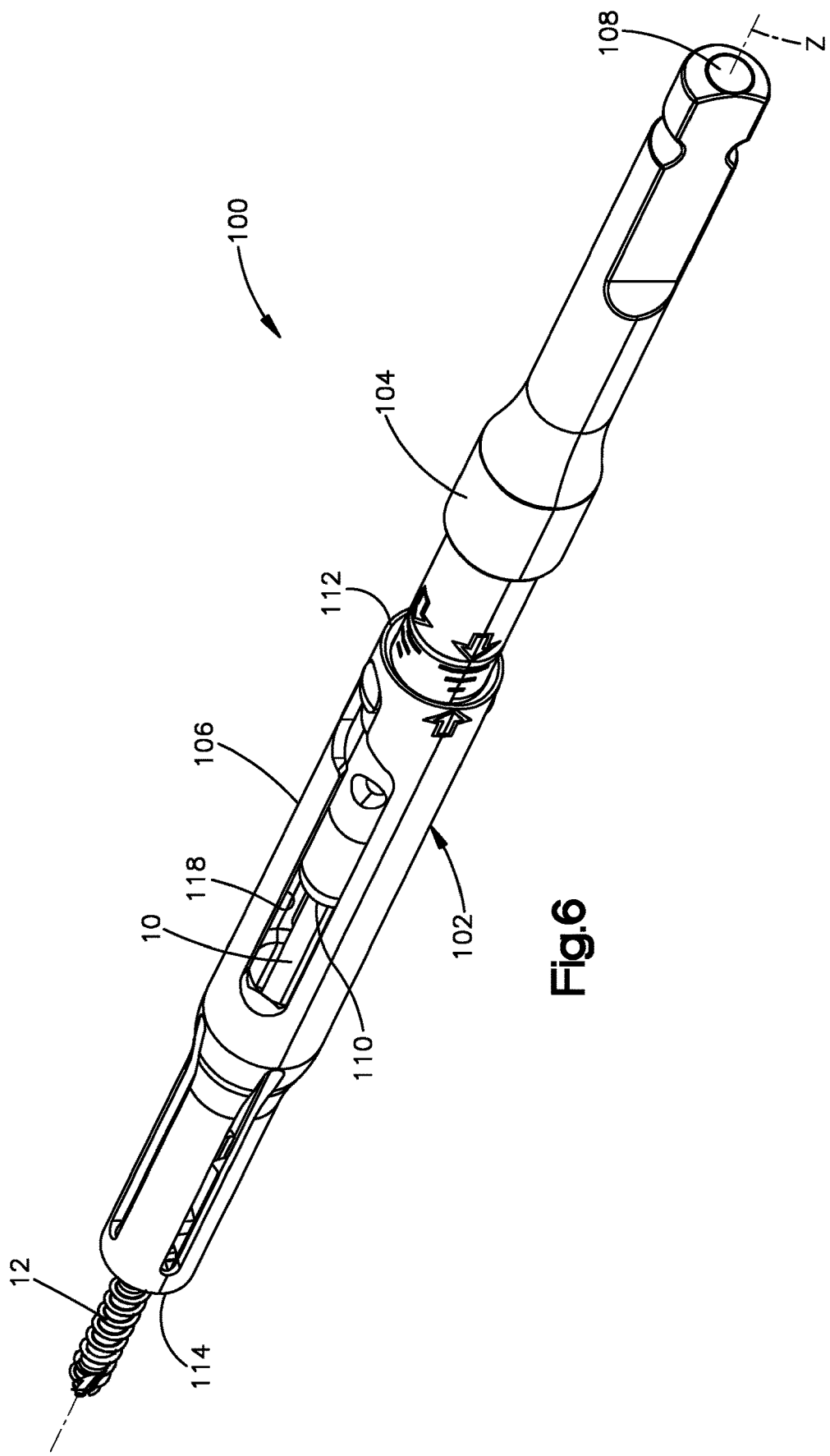
FIG. 6 is a perspective view of a driving tool that includes a drive adapter and a drive sleeve, wherein the driving tool configured for inserting the fixation element of FIG. 1 into a bone, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

FIG. 1 illustrates a fixation element 2 for insertion into a bone according to an embodiment of the present disclosure. The fixation element 2 can be elongate along a central axis 4 and can include a proximal end 6 and a distal end 8 spaced from the proximal end 6 along the central axis 4. The central axis 4 can define a longitudinal direction X of the fixation element 2. A radial direction R can be perpendicular to the longitudinal direction X. A distal direction can be defined as extending from the proximal end 6 of the fixation element 2 toward the distal end 8 thereof and being parallel with the central axis 4. The fixation element 2 can include a removable member 10 coupled to an anchor member 12 that is located distally of the removable member 10 along the central axis 4. The removable member 10 can be coupled to the anchor member 12 in such a manner so as to facilitate insertion of the anchor member 12 to a desired depth within a target bone. The fixation element 2 can be configured to receive axial and rotational drive forces to facilitate insertion into the target bone. The fixation element 2 can be configured such that, once the anchor member 12 reaches a predetermined final depth within the target bone, the removable member 10 detaches cleanly from the anchor member 12, leaving the anchor member 12 inserted within the target bone at the final depth.

The removable member 10 can include a proximal end 14 and a distal end 16 spaced from the proximal end 14 along the central axis 4. The proximal end 14 of the removable member 10 can form the proximal end 6 of the fixation element 2. The anchor member 12 can include a proximal end 18 and a distal end 20 spaced from the proximal end 18 along the central axis 4. The distal end 20 of the anchor member 12 can form the distal end 8 of the fixation element 2.

The removable member 10 can be joined to the anchor member 12 at an attachment location 21 positioned therebetween. The attachment location 21 may be characterized as an "interface" or "joint" between the removable member 10 and the anchor member 12 and may be configured to facilitate detachment of the removable member 10 from the anchor member 12 responsive to a predetermined condition of operation. For example, the predetermined condition of operation can be the predetermined final depth of the anchor member 12 or a force differential, such as a torque differential, exerted between the removable member 10 and the anchor member 12, by way of non-limiting example.

The fixation element 2 can include one or more engagement elements 22 configured to engage force transmission elements of a driving tool and transfer rotational driving forces from the driving tool to the fixation element 2. In this manner, the anchor member 12 can be driven into the target bone by the driving tool. The engagement elements 22 can be located on one or both of the removable member 10 and the anchor member 12 of the fixation element 2.

The removable member 10 and the anchor member 12 can be monolithic with one another. In such embodiments, the attachment location 21 can include a neck 23 joining the distal end 16 of the removable member 10 and the proximal end 18 of the anchor member 12. The removable member 10 can include a post 24 located proximally of the neck 23. The post 24 can be cylindrical, as depicted; however, other post geometries are within the scope of the present disclosure. The neck 23 can have a reduced width in relation to a remainder of the removable member 10, including the post 24, and can be configured to fracture responsive to the predetermined condition of operation, as discussed in more detail below. However, other frangible or detachable couplings can be utilized to join the anchor member 12 and the removable member 10.

As illustrated, the anchor member 12 can be a bone screw 25 having a head 26 and a shaft 28 extending distally from the head 26 along the central axis 4. The shaft 28 can terminate distally at a pointed tip 30 that can also be characterized as the distal end 20 of the anchor member 12 and the distal end 8 of the fixation element 2. The pointed tip 30 can be configured to penetrate a cortical wall of bone. The shaft 28 can include a helical thread 32 extending between the head 26 and the tip 30. The pointed tip 30 and the thread 32 can provide the bone screw 25 with self-drilling functionality. Additionally, at least one flute 34 can be formed in the shaft 28 adjacent the pointed tip 30, providing the bone screw 25 with self-tapping functionality through both cortical bone material and cancellous bone material.

The engagement elements 22 of the fixation element 2 can include a plurality of projections extending radially from one or both of the removable member 10 and the anchor member 12, as also shown in FIG. 2. For example, the anchor member 12 can include a first plurality of projections 36 that are located adjacent the proximal end 18 of the anchor member 12 and extend radially outward from the anchor member 12. In embodiments where the anchor member 12 is a bone screw 25, the projections 36 can form the structure of the head 26. In the illustrated embodiment of FIG. 1, the first plurality of projections 36 can include four (4) projections 36 spaced at 90° intervals about the central axis 4

As shown in FIG. 3, the first plurality of projections 36 can form a cross pattern when viewed from the central axis 4. Each of the first plurality of projections 36 can include a pair of opposed lateral surfaces 38a, 38b and a peripheral surface 40 extending between the pair of opposed lateral surfaces 38a, 38b. One of the lateral surfaces 38a can be on a rotationally leading side 42 of the associated projection 36 and the other of the lateral surfaces 38b can be on a rotationally trailing side 44 of the associated projection 36. Each leading lateral surface 38a can form a right angle (90°) with the trailing lateral surface 38b of the preceding projection 36. The boundary between each adjacent rotationally leading and trailing side 44, 42 may optionally be radiused to reduce stress concentrations within the anchor member 12.

The lateral surfaces 38a, 38b can each extend in the longitudinal direction X. In some embodiments, the lateral surfaces 38a, 38b can each be substantially planar. In such embodiments, each of the lateral surfaces 38a, 38b can extend along a plane defined by a first direction that is parallel with the longitudinal direction X and a second direction that is perpendicular to the first direction and parallel with the radial direction R. In embodiments where the threading 32 of the anchor member 12 is configured according to the "right hand rule," the rotationally leading side 42 of each projection 36 faces counterclockwise when viewed from the central axis 4 at a location distal the distal end 8 of the fixation element 2, while the rotationally trailing side 44 of each projection 36 faces clockwise when viewed from the central axis 4 at a location distal the distal end 8 of the fixation element 2. Thus, the trailing lateral surfaces 38b can directly receive the rotational driving force from the driving tool.

The engagement elements 22 of the fixation element 2 can also include a second plurality of projections 46 extending radially from the removable member 10. The second plurality of projections 46 can be located adjacent the attachment location 21 and can also include four (4) projections 46 spaced at 90° intervals about the central axis 4. As shown in FIG. 4, the second plurality of projections 46 can also form a cross pattern. In the illustrated embodiment, the second plurality of projections 46 can be aligned with the first plurality of projections 36 about the central axis 4. However, it is to be appreciated that, in other embodiments (not shown), the first and second plurality of projections 36, 46 can be offset from each other about the central axis 4.

Each of the second plurality of projections 46 can include a pair of opposed lateral surfaces 48a, 48b and a peripheral surface 50 extending between the pair of opposed lateral surfaces 48a, 48b. One of the lateral surfaces 48a of the second plurality of projections 46 can be on a rotationally leading side 52 of the associated projection 46 and the other of the lateral surfaces 48b can be on a rotationally trailing side 54 of the associated projection 46. Each leading lateral surface 48a can form a right angle (90°) with the trailing lateral surface 48b of the preceding projection 46.

The lateral surfaces 48a, 48b of the second plurality of projections 46 can each extend in the longitudinal direction X. The lateral surfaces 48a, 48b of the second plurality of projections 46 can each be substantially planar. For example, each of the lateral surfaces 48a, 48b can extend along a plane defined by a third direction that is parallel with the longitudinal direction X and a fourth direction that is perpendicular to the third direction and parallel with the radial direction R. In embodiments where the second plurality of projections 46 is aligned with the first plurality of projections 36 about the central axis 4, the first and third directions are parallel with one another, and the second and fourth directions are parallel with one another. Thus, the trailing lateral surfaces 48b can directly receive the rotational driving force from the driving tool.

Furthermore, when the first and second plurality of projections 36, 46 are aligned about the central axis 4, a projection 36 of the first plurality and an associated projection 36 of the second plurality may be characterized as a pair of projections 36, 46. Moreover, the lateral surfaces 38a, 38b, 48a, 48b on the same side 42, 44, 52, 54 of one of the pairs of projections 36, 46 may be characterized as a pair of lateral surfaces 38, 48. Accordingly, a pair of lateral surfaces 38, 48 can be engaged by the same force transmission element of the driving tool, as set forth in more detail below.

Optionally, the post 24 of the removable member 10 can have a radius $R_1$ that is substantially equivalent to an inner radius $R_2$ of each of the lateral surfaces 48a, 48b of the second plurality of projections 46, allowing each lateral surface 48a, 48b of the second plurality of projections 46 to be contiguous with the lateral surface 48b, 48a of the successive projection 46 about the central axis 4. Additionally, an inner radius $R_3$ of each of the lateral surfaces 38a, 38b of the first plurality of projections 36 can be substantially equivalent to the inner radius $R_2$ of each of the lateral surfaces 48a, 48b of the second plurality of projections 46. In this manner, the force transmission elements of the driving tool can fit snuggly against each associated pair of lateral surfaces. Thus, the force transmission elements of the driving tool can apply substantially the same amount of torque to each associated pair of projections 36, 46, and thus the same amount of torque to anchor member 12 and the removable member 10 prior to the predetermined condition of operation.

FIG. 5 depicts an enlarged sectional view of the attachment location 21 and the engagement elements 22 of the fixation element 2. As described above, the attachment location 21 can include a neck 23 having a reduced width in relation to a width of the remainder of the removable member 10. In this manner, the fixation element 2 is configured to fracture cleanly at the neck 23 responsive to the predetermined condition of operation.

During insertion of the fixation element 2 into bone in a first mode of operation, the force transmission elements of the driving tool can apply a rotational force to the pairs of lateral surfaces 38, 48, resulting in a driving torque applied direction each of the anchor member 12 and the removable member 10. In a second mode of operation, the force transmission elements of the driving tool can disengage from the trailing lateral surfaces 38b of the projections 36 of the anchor member 12 apply substantially all of the rotational driving force to the trailing lateral surfaces 48b of the projections 46 of the removable feature 10, creating a differential in the amount of torque applied between the removable member 10 and the anchor member 12.

The fixation element 2 can be configured such that stress from the torque differential is concentrated within the neck 23, causing mechanical failure (i.e., fracture) at the neck 23 when the torque differential exceeds a predetermined value. The fixation element 2 and the driving tool can be cooperatively configured such that the torque differential exceeds the predetermined value when the predetermined condition of operation occurs.

The geometries of the distal end 16 of the removable member 10, the neck 23, and the proximal end 18 of the anchor member 12 can be configured to ensure that fracture of the fixation element 2 occurs at the neck 23. In particular, the neck 23, the proximal end 18 of the anchor member 12, and the distal end 16 of the removable member 10 can be cooperatively shaped and sized to concentrate stresses within the neck 23 when a torque differential is imparted between the removable member 10 and the anchor member 12. For example, the peripheral surface 50 of each of the projections 46 of the removable member 10 can include a rear segment 55, an intermediate segment 56 located distally of the rear segment 55, and a front segment 58 located distally of the intermediate segment 56. As shown, the intermediate segment 56 can be substantially parallel with the central axis 4. The front segment 58 can taper inwardly toward the central axis 4 in the distal direction. As shown, the front segment 58 can taper distally in a manner so as to be contiguous with the neck 23.

The peripheral surface 40 of each of the projections 36 of the anchor member 12 can include a rear segment 60, one or more intermediate segments 62 located distally of the rear segment 60, and a front segment 64 located distally of the one or more intermediate segments 62. The rear segments 60 can also be characterized as the proximal-most end of the associated projections 36, of the head 26, and of the anchor member 12. At least a portion of the rear segment 60 can be located proximally of the neck 23 so that, after the neck 23 fractures responsive to the predetermined condition of operation, and after the removable member 10 is removed, the fractured region of the anchor member 12 preferably does not include any protrusion, such as a nub, shard, or jagged edge, that extends proximally beyond the rear segment 60. It is to be appreciated that any such nub, shard, jagged edge, or other protrusion extending proximally beyond the rear segment 60 could pierce, abrade, or otherwise damage soft tissue of the patient overlying the inserted anchor member 12. The foregoing geometries of the removable member 10 and the anchor member 12 adjacent the neck 23 may substantially reduce the likelihood of such occurrences.

With continued reference to FIG. 5, the shaft 28 of the anchor member 12 can include a tapered portion 66 located distally of and adjacent the head 26. The tapered portion 66 of the shaft 28 can taper inwardly toward the central axis in the distal direction. The tapered portion 66 can be sized and configured to provide the anchor member 12 with a gradual transition between the diameter $D_2$ of the shaft 28 and an increasing diameter of the front segment 64 of the head 26 as the anchor member 12 is inserted and the head 26 is seated within the target bone. Stated differently, the tapered portion 66 provides gradual seating of the head 26 of the anchor member 12, as well as reduces hoop stress during insertion. The tapered portion 66 can reduce the likelihood of the target bone splitting or cracking at or adjacent the location where the anchor member 12 is inserted into the bone. The angle of taper $\alpha$ of the tapered portion 66, relative to the central axis 4, can be constant or can vary along the distal direction. By way of non-limiting example, in some embodiments, the angle of taper $\alpha$ can be constant and can be in the range of about 0° and about 45°. In other embodiments, the angle of taper $\alpha$ can be between about 5° and about 25°. Additionally, the front segment 64 of the peripheral surface 40 of each of the first plurality of projections 36 can have a convex arcuate profile to further provide gradual seating of the head 26 of the anchor member 12 within the target bone. It is to be appreciated that the tapered portion 66 may be omitted.

The predetermined condition of operation, which triggers detachment of the removable member 10 from the anchor member 12, can be subject to a number of factors, including, but not limited to, the identity, size, shape and/or density of the target bone; the desired depth, axial and/or rotational insertion speed, and/or angle of insertion of the anchor member 12 into the target bone; the material condition and/or optional heat treatment of any one of the fixation element 2, the removable member 10, and/or the anchor member 12; the angle at which the front segment 58 and/or the rear segment 60 of the projections 46 are oriented relative to the central axis 4, etc. The dimensions and material composition of the fixation element 2, including the neck 23, for example, can be tailored to account for the foregoing factors. It is to be appreciated that the predetermined condition of operation can also be triggered unilaterally by a user, such as a physician, by manually fracturing the neck 23.

The removable member 10 can have a length $L_1$ in the range of about 20 mm to about 50 mm or greater, measured from the proximal end 14 to the distal end 16 of the removable member 10. In some embodiments, the removable member 10 can have length $L_1$ in the range of about 20 mm to about 35 mm. In further embodiments, the removable member 10 can have a length $L_1$ in the range of about 35 mm to about 50 mm. In additional embodiments, the removable member 10 can have length $L_1$ greater than 50 mm or even greater than 100 mm. In other embodiments, the removable member 10 can have a length $L_1$ in the range of about 1 mm to about 20 mm, including a range between about 1 mm and about 5 mm.

The post 24 of the removable member 10 can have a diameter $D_1$ in the range of about 0.5 mm to about 4.0 mm. In some embodiments, the post 24 can have a diameter $D_1$ in the range of about 0.5 mm to about 0.8 mm. In other embodiments, the post 24 can have a diameter $D_1$ in the range of about 0.8 mm to about 1.5 mm. In additional embodiments, the post 24 can have a diameter $D_1$ in the range of about 1.5 mm to about 2.5 mm. In further embodiments, the post 24 can have a diameter $D_1$ in the range of about 2.5 mm to about 4.0 mm. In yet additional embodiments, the post 24 can have a diameter $D_1$ greater than 4.0 mm. It is to be appreciated that in embodiments where the diameter $D_1$ of the post 24 is in the range of about 0.8 mm to about 2.5 mm, the post 24 can provide the benefit of being engagable and drivable by a wire drive, such as a Kirschner wire ("K-wire") drive.

The shaft 28 of the anchor member 12 can have a diameter $D_2$ in the range of about 0.5 mm to about 4.0 mm or greater. For example, the shaft 28 can have a diameter $D_2$ in the range of about 0.5 mm to about 1.5 mm. In other embodiments, the shaft 28 can have a diameter $D_2$ in the range of about 1.5 mm to about 2.0 mm. In other embodiments, the shaft 28 can have a diameter $D_2$ in the range of about 2.0 mm to about 2.7 mm. In additional embodiments, the shaft 28 can have a diameter $D_2$ in the range of about 2.7 mm to about 3.5 mm. In further embodiments, the shaft 28 can have a diameter $D_2$ in the range of about 3.5 mm to about 4.0 mm. In yet additional embodiments, the shaft 28 can have a diameter $D_2$ greater than 4.0 mm. Additionally, the threads 32 can be formed of a size and thread pitch that facilitates smooth insertion as well as self-drilling and/or self-tapping functionality.

The fixation element 2 can be formed of a material that includes one or more of a titanium-aluminum-vanadium alloy (such as Ti-6Al-4V, also referred to as "TAV"), a titanium-aluminum-niobium alloy (such as Ti-6Al-7Nb, commonly referred to as "TAN"), steel, such as stainless steel, or any alloys comprising the foregoing thereof. In additional embodiments, the fixation element 2 can be formed of thermoplastic polymer, such as a polyetheretherketone (PEEK) material, although it is to be appreciated that, in such embodiments, pre-drilling can be required before inserting the anchor member 12 into bone. It is to be appreciated that the fixation elements 2 can be composed of any suitable biocompatible materials known in the art.

In one non-limiting example embodiment, the post 24 can have a diameter $D_1$ of about 1.4 mm and a length $L_1$ of at least about 20 mm; the shaft 28 of the anchor member 12 can have a diameter $D_2$ of about 2.0 mm; and the neck 23 can have a diameter $D_3$ of about 0.8 mm. In this example, the neck 23 can fracture when the torque differential between the removable member 10 and the anchor member 12 is about 0.93 N*m. Furthermore, through numerous tests, the inventors discovered, surprisingly and unexpectedly, that, at the foregoing dimensions of this example embodiment, the fixation element 2 composed of TAN produced a flatter, less jagged fracture profile in the neck 23 than other materials, reducing the likelihood of nubs, shards, or other protrusions projecting proximally beyond the rear surface 60 of the head 26 of the anchor member 12. The fixation element 2 sized and configured according to the foregoing example embodiment can be advantageously suited for insertion within a "lesser ray" of a foot, such as is common in certain hallus valgus correction procedures, including osteotomies. It is to be appreciated that the foregoing example embodiment can also be advantageously suited for other surgical procedures.

It is to be appreciated that the fixation element 2 disclosed herein is not limited to any particular size, as the fixation element 2 and its constituent components can be scaled to virtually any size to accommodate any use, including use in longbones, by way of non-limiting example. Accordingly, at any size of the fixation element 2, the diameter $D_1$ of the post 24, the diameter $D_2$ of the shaft 28, the diameter $D_3$ of the neck 23, and/or the size of any or all of the engagement elements 22 can each be tailored to achieve detachment of the removable member 10 when the predetermined condition of operation occurs.

It is also to be appreciated that while the fixation element 2 depicted in FIGS. 1-4 illustrate the engagement elements 22 of each of the removable member 10 and the anchor member 12 forming a cross-pattern, any geometry of the engagement elements is within the scope of the present disclosure. For example, in other embodiments (not shown), the engagement elements 22 can form a hex pattern, a star pattern, or any other pattern conducive to receiving a driving torque from the drive tool and transmitting the torque to the fixation element 2. In further embodiments, instead of projections 36, 46 extending from the anchor member 12 and the removable member 10, respectively, the head 26 of the anchor member 12 and an associated head of the removable member 10 can each have a generally circular cross-sectional profile in a plane orthogonal to the central axis 4, wherein the engagement elements 22 include recesses extending into the respective heads in the radial direction R. In such embodiments, the respective circular heads of the anchor member 12 and the removable member 10 can each include two or more recesses evenly spaced from each other about the central axis 4. In further embodiments, other geometries of the engagement elements 22 are contemplated.

FIG. 6 illustrates an insertion system 100 for inserting the fixation element into 2. The system 100 includes a driving tool 102 that is configured to receive the fixation element 2 and drive the fixation element 2 into the target bone until the fixation element 2 reaches a predetermined depth within the bone. The driving tool 102 can define a longitudinal axis Z and can include a drive adapter 104 and a drive sleeve 106 that is carried by the drive adapter 104. The drive adapter 104 can include a proximal end 108 and a distal end 110 separated from the proximal end along the longitudinal axis Z. The drive sleeve 106 can include a proximal end 112 receivable over the distal end 110 of the drive adapter 104. As shown, the distal end 110 of the drive adapter 104 can be received within the drive sleeve 106. The drive sleeve 106 can include a distal end 114 separated from the sleeve proximal end 112 along the longitudinal axis Z. With respect to the drive tool 2, and also with respect to the fixation element 2 received therein, the distal direction can be defined as extending from the proximal end 108 of the drive adapter toward the distal end 114 of the drive sleeve 106 and being parallel with the longitudinal axis Z.

The drive adapter 104 can be translatable relative to the drive sleeve 106 along the longitudinal axis Z between an initial position and a fully inserted position, the latter position occurring when the anchor member 12 is inserted within the target bone at a predetermined final depth. The drive adapter 104 can be configured to apply the axial driving force directly to the fixation element 2, and the drive sleeve 106 can be configured to apply the rotational driving force directly to the fixation element 2.

The fixation element 2 can be at least partially received within and coupled to the drive adapter 104. For example, the distal end 110 of the drive adapter 104 can include a chuck 116 (see FIG. 7) configured to receive the proximal end 14 of the post 24 of the fixation element 2. The drive sleeve 106 can define a central bore 118 and can have a length sufficient to receive and surround a majority of the fixation element 2 when the fixation element 2 is loaded within the chuck 116. Accordingly, the drive sleeve 106 may be termed a "receiving member." In the initial position, the proximal end 14 of the removable member 10 of the fixation element 2 can be received within and coupled to the drive adapter 104 while only the shaft 28 of the anchor member 12 extends beyond a distal end 114 of the drive sleeve 106. When the drive sleeve 106 is in the fully inserted position relative to the drive adapter 104, the entire anchor member 12, except for a portion of the head 26, can be located distally of the distal end 114 of the drive sleeve 106, as described in more detail below.

Figure 7:
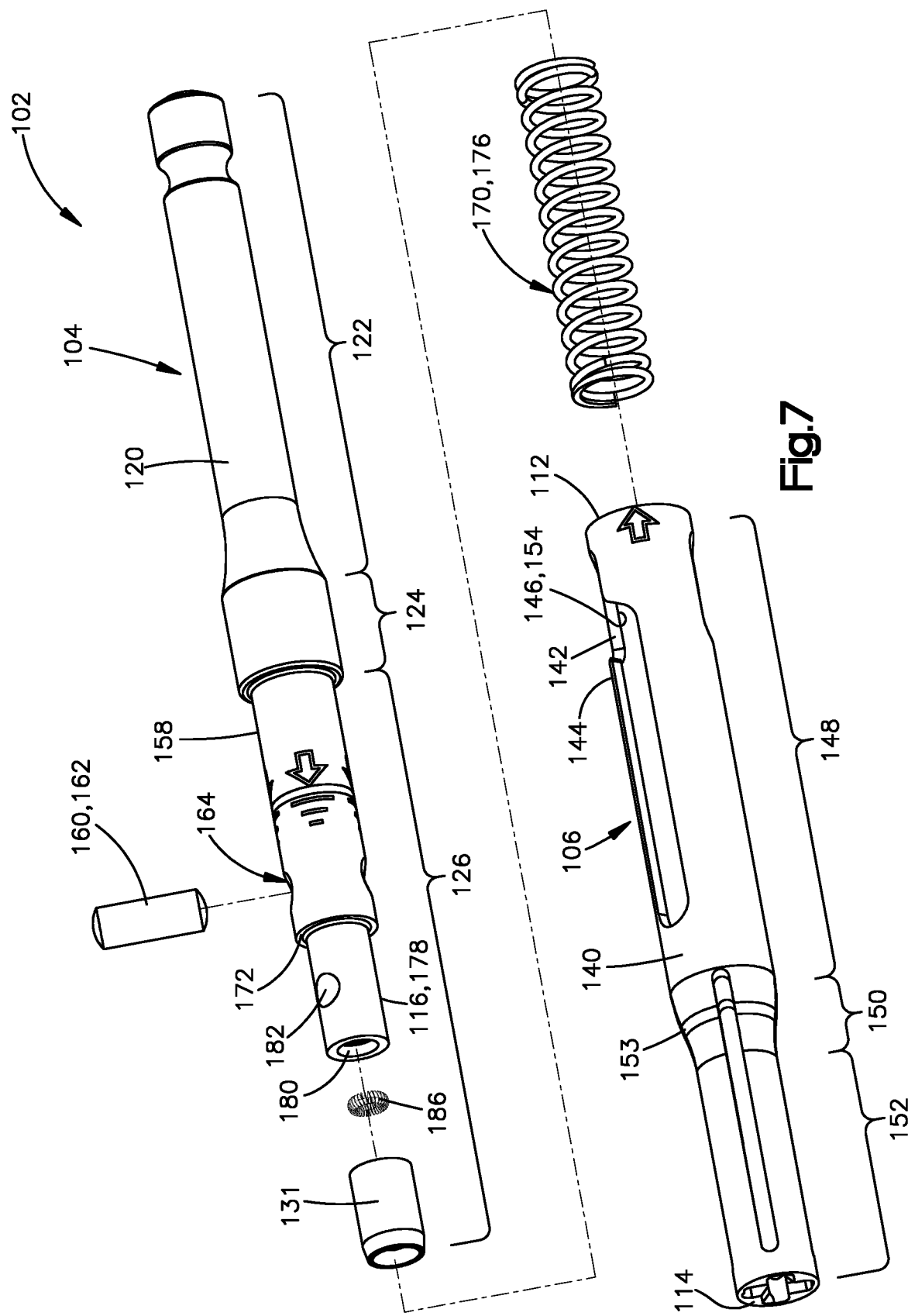
FIG. 7 is a perspective, exploded view of the driving tool of FIG. 6.

Referring now to FIG. 7, the drive adapter 104 can include a body 120, also termed an "adapter body," that can be generally cylindrical, although other geometries are within the scope of the present disclosure. The adapter body 120 may be characterized as having a proximal portion 122 adjacent the adapter proximal end 108, a distal portion 126 adjacent the adapter distal end 110, and an intermediate portion 124 located longitudinally between the proximal portion 122 and distal portion 126.

It is to be appreciated that a proximal end 128 of the adapter body 120 can form the proximal end 108 of the drive adapter 104. The adapter body 120 can have a distal end 130 spaced from the proximal end 128 of the adapter body 120 along the longitudinal axis Z. The distal end 130 of the adapter body 120 can coincide with a distal end of the chuck 116. An end cap 131 can be coupled to the chuck 116, such that a distal end 132 of the end cap 131 can form the distal end 110 of the drive adapter 104. Thus, the proximal end 108 of the drive adapter 104 can be synonymous with the proximal end 128 of the adapter body 120; the distal end 130 of the adapter body 120 can be synonymous with the distal end of the chuck 116; and the distal end of the drive adapter 104 can be synonymous with the distal end of the end cap 131.

The proximal portion 122 of the adapter body 120 can define an outer surface 144 and one or more grip features formed in the outer surface 144. The one or more grip features can provide purchase for a user's hand or a power tool for operating the driving tool 102 to insert the anchor member 12 into the target bone. By way of non-limiting example, the grip features can include a platform 136 recessed into the adapter body 120 adjacent the proximal end 108 thereof. The platform 136 can extend in a direction parallel with the longitudinal axis Z and can be contiguous with the outer surface 144 of the adapter body 120. As shown, the platform 136 can be substantially planar, although it is to be appreciated that other geometries are within the scope of the present disclosure. The grip features can also include an annular recess 138 formed in the outer surface 144 of the adapter body 120 at or adjacent the proximal end 108 thereof. The adapter body 120 can include and/or carry one or more coupling elements for coupling with various components of the drive sleeve 106 and the fixation element 2.

The drive sleeve 106 can have a sleeve body 140 having a tubular, generally cylindrical shape and defining the sleeve central bore 118, which extends from the proximal end 112 to the distal end 114 of the sleeve body 140. Accordingly, the sleeve body 140 may be characterized as a "tubular body." The sleeve body 140 can include a sleeve wall 142 extending radially between an outer surface 144 of the sleeve body 140 and an inner surface 146 of the sleeve body 140. The sleeve body 140 may be characterized as having a proximal portion 148 adjacent the proximal end 112 of the drive sleeve 106, a distal portion 152 adjacent the sleeve distal end 114, and an intermediate portion 150 located longitudinally between the proximal portion 148 and distal portion 152. The outer surface 144 of the sleeve body 140 in the distal portion 152 thereof can have a reduced diameter in relation to that of the outer surface 144 in the proximal portion 148. The intermediate portion 150 of the sleeve body 140 may be characterized as tapering in the distal direction. Stated differently, the outer surface 144 of the sleeve body 140 may include a taper 153 coincident with the intermediate portion 150 of the sleeve body 140.

The drive sleeve 106 can also include one or more attachment elements that are complementary with and are configured to directly or indirectly engage with at least one of the one or more coupling elements of the adapter body 120. For example, the proximal portion 148 of the drive sleeve 106 can include a first attachment element 154 configured to engage a first coupling element 156 of the distal portion 126 of the adapter body 120. In particular, the first attachment element 154 of the sleeve body 140 can include the inner surface 146 of the sleeve body 140 within the proximal portion 148 thereof, as shown in FIG. 8, which illustrates a sectional view of the driving tool 2 along the longitudinal axis Z. With continued reference to FIGS. 7 and 8, the associated first coupling element 156 of the adapter body 120 can include a cylindrical outer surface 158 of the adapter body 120 within the distal portion 126 thereof. The cylindrical outer surface 158 of the distal portion 126 of the adapter body 120 and the inner surface 146 of the proximal portion 148 of the sleeve body 140 can be cooperatively sized and configured such that the inner surface 146 of the sleeve body 140 at the proximal portion 148 thereof slidably engages with and translates over the cylindrical outer surface 158 of the distal portion 126 of the adapter body 120 during use of the driving tool 102. For example, the cylindrical outer surface 158 of the distal portion 126 of the adapter body 120 can have a diameter substantially equivalent to or slightly smaller than a diameter of the inner surface 146 of the proximal portion 148 of the sleeve body 140, facilitating translational engagement between the distal portion 126 of the adapter body 120 and the proximal portion 148 of the sleeve body 140.

The distal portion 126 of the adapter body 120 can also carry a second coupling element 160, which can be configured to retain the drive sleeve 106 on the drive adapter 104 during operation. The second coupling element 160 can include a pin 162 received in a first transverse bore 164 extending through the distal portion 126 of the adapter body 120 and intersecting the longitudinal axis Z of the driving tool 102. The pin 162 can have a length greater than the diameter of the cylindrical outer surface 158 of the distal portion 126 of the adapter body 120, such that each opposed end of the pin 162 protrudes from the cylindrical outer surface 158.

The one or more attachment elements of the drive sleeve 106 can include a pair of opposed slots 166 each formed through the sleeve wall 142 and extending longitudinally along at least a portion of the sleeve body 140. When the proximal end 112 of the sleeve body 140 is received over the cylindrical outer surface 158 of the distal portion 126 of the adapter body 120, the opposed ends of the pin 162 can extend radially through the pair of opposed slots 166 of the sleeve body 140 in a manner retaining the proximal portion 148 of the drive sleeve 106 on the distal portion 126 of the drive adapter 104. The opposed ends of the pin 162 can each have a diameter substantially equivalent to or slightly less than a circumferential width of each of the pair of opposed slots 166, such that the pin 162 can translate along the slots 166 during use of the driving tool 102. In this manner, the orientation of the opposed slots 166 along the sleeve body 140 can govern at least an extent of translational and rotational movement of the drive sleeve 106 relative to the drive adapter 104, as set forth more fully below. Accordingly, the slots 166 may be termed "guide slots," and the pin 162 may be termed a "follower pin" or a "follower."

The driving tool 102 can include a biasing member 170 biasing the drive sleeve 106 in the initial position relative to the drive adapter 104. The biasing member 170 can be disposed between a first shoulder 172 located on the distal portion 126 of the adapter body 120 and a second, opposed shoulder 174 formed on the inner surface 146 of the sleeve body 140, as shown in FIG. 8. The first shoulder 172 can be positioned distally of the first transverse bore 164. The second shoulder 174 can be located proximally of the taper 153 of the outer surface 144 of the sleeve body 140, and thus may be characterized as being located in the proximal portion 148 of the sleeve body 140, as shown in the illustrated embodiment. Alternatively, the second shoulder can be located in the intermediate portion 150 or the distal portion 152 in other embodiments. The first shoulder 172 can substantially face the distal direction and the second shoulder can substantially face the proximal direction. The biasing member 170 can include a compression spring 176, although other types of biasing members 170 are within the scope of the present disclosure.

The one or more coupling elements of the adapter body 120 can include a third coupling element 178, which can be configured to receive the proximal end 14 of the post 24 of the fixation element 2. The third coupling element 178 can include the chuck 116, which can define a central bore 180 formed in the distal portion 126 of the adapter body 120. The central bore 180 can extend from the distal end 130 of the adapter body 120 in the proximal direction. The central bore 180 can optionally intersect a second transverse bore 182 extending through the distal portion 126 of the adapter body 120. The second transverse bore 182 can be positioned longitudinally between the first transverse bore 164 and the distal end 130 of the adapter body 120. The second transverse bore 182 can also be located distally of the first shoulder 172 on the attachment body 120. In the illustrated embodiment, a central axis of the second transverse bore 182 can optionally be offset by an angle of about 45° from a central axis 184 of the first transverse bore 164 about the longitudinal axis Z. However, in other embodiments (not shown), the first and second transverse bores 164, 182 can be parallel with one another, or can have any other orientation relative to one another. As shown in FIGS. 7 and 8, the second transverse bore 182 can coincide with the terminal end of the central bore 180 of the chuck 116. Thus, a rear inner surface of the second transverse bore 182 can transmit the axial driving force to the anchor member 12 through the post 24. The central bore 180 can have an inner diameter substantially equivalent to or slightly greater than the diameter $D_1$ of the post 24 so that the proximal end 14 of the post 24 can be received (i.e., "loaded") within the central bore 180.

The third coupling element 178 of the drive adapter 104 can include a retention element 186 configured to hold the post 24 of the fixation element 2 within the central bore 180 of the chuck 116. The retention element 186 can impart the post 24 with a retention force (i.e., in the proximal direction) that is at least greater than the gravitational force of the fixation element 2, thus preventing the post 24 from sliding out of the central bore 180 under gravity. The retention force can also be sufficient to prevent the post 24 from sliding out of the central bore 180 due to additional inertial forces associated with regular use of the driving tool 102. Accordingly, the retention element 186 can allow a physician to insert the fixation element 2 at an inclined angle without the post 24 sliding out of the chuck 116. The retention element 186 can be disposed within the end cap 131 mounted on the chuck 116.

FIG. 9A is a magnified view of the portion of the driving tool 102 indicated by dashed rectangle B of FIG. 8. The end cap 131 can define a central bore 188 sized to receive the post 24. It is to be appreciated that any manner of coupling the end cap 131 to the chuck 116 is within the scope of the embodiments disclosed herein. The retention element 186 can be received within an annular recess 189 formed in the central bore 189 of the chuck 116 at the distal end 130 thereof. The retention element 186 can abut against a proximal end 133 of the end cap 131 in a manner retaining the retention element 186 in the annular recess 189. The retention element 186 can be a spring 192 having a resilient body with an inner diameter slightly smaller than the diameter $D_1$ of the post 24 to provide the retention force to the post 24. The spring 192 can be a polymeric ring member that is compressed within the annular recess 189 by the proximal end 133 of the end cap 131 when the end cap 131 is fully seated in relation to the chuck 116 so as to provide the spring 192 with the inner diameter slightly less than the diameter $D_1$ of the post 24. However, it is to be appreciated that other types of retention elements for preventing the post 24 from slipping out of the cylindrical bore 180 during normal use of the driving tool 102 are within the scope of the present disclosure. By way of non-limiting example, the retention element 186 can include a circular coil spring, a rubber ring seal sized to provide a friction fit with the post 24, a spring-loaded ball and groove detent arrangement on the post 24 and central bore 188, respectively, and a tapered distal end of the chuck 116 sized to pinch onto the post 24.

FIG. 9B illustrates an alternative end cap 131 arrangement, wherein the end cap 131 defines a sleeve received over the chuck 116. In this arrangement, the spring 192 can be disposed within the central bore 188 of the end cap 131 between the distal end 130 of the chuck 116 and an opposed abutment surface 191 formed within the central bore 188 of the end cap 131. The abutment surface 191 can be oriented perpendicular to the longitudinal axis Z of the driving tool 102. The spring 192 can be compressed between the distal end 130 of the chuck 116 and the abutment surface 190 when the end cap 131 is fully seated in relation to the chuck 116 so as to provide the spring 192 with the inner diameter slightly less than the diameter $D_1$ of the post 24.

Referring again to FIG. 8, drive sleeve 106 can include force transmission elements 200 located in the distal portion 152 of the sleeve body 140. The force transmission elements 200 can be formed on the inner surface 146 of the sleeve body 140 and can be configured to engage the engagement elements 22 of the fixation element 2 in a manner providing the rotational driving force to the fixation element 2, as discussed in more detail below.

Figure 10:
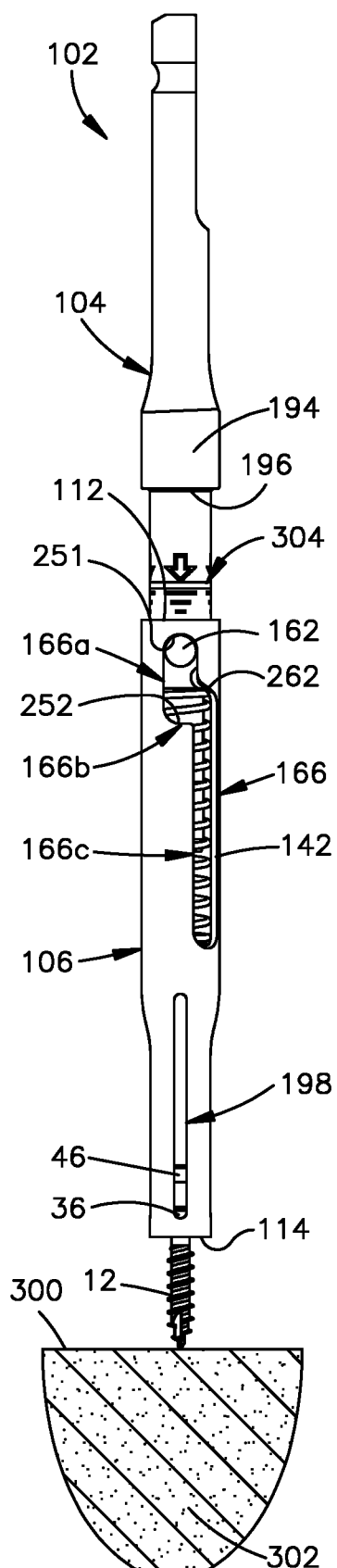
FIG. 10 is a side view of the driving tool of FIG. 6 positioned adjacent a bone, wherein the drive adapter and the fixation element are depicted in an initial position relative to the drive sleeve.
Figure 11:
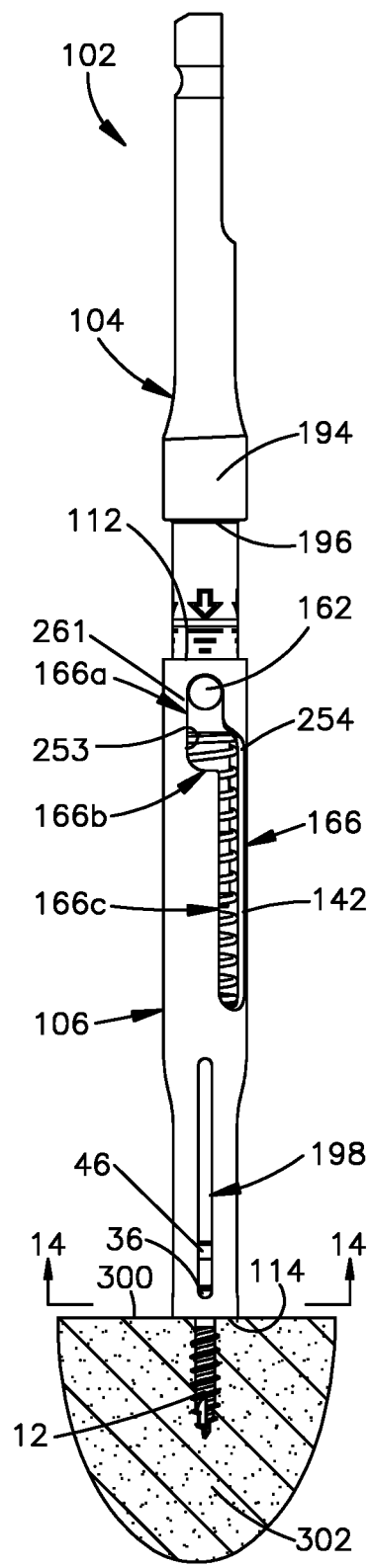
FIG. 11 is a side view of the driving tool of FIG. 10, with the fixation element partially inserted in the bone, and the drive adapter and the fixation element remaining in the initial position relative to the drive sleeve.
Figure 12:
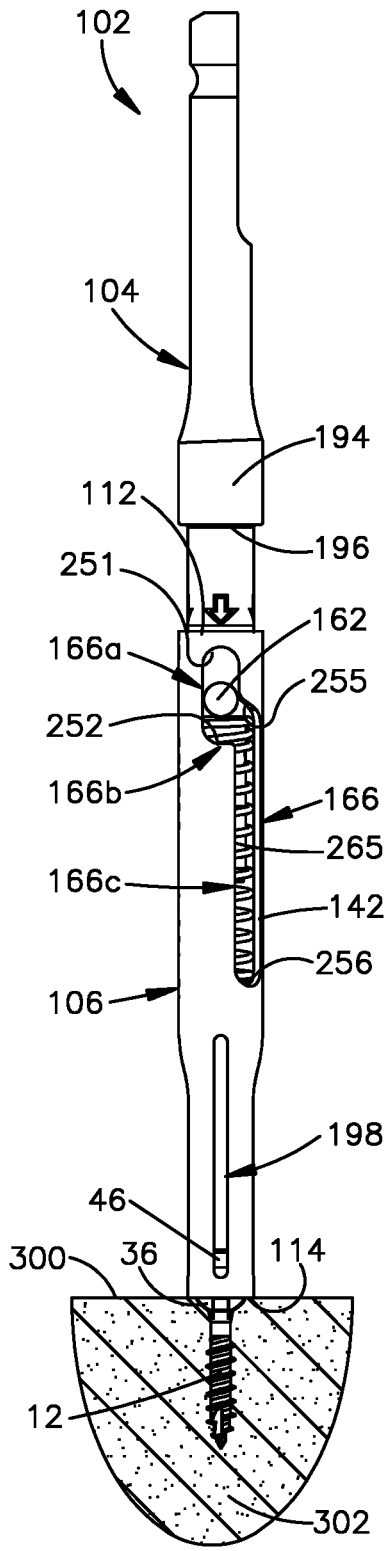
FIG. 12 is a side view of the driving tool of FIG. 11, with the fixation element fully inserted in the bone, and the drive adapter and the fixation element depicted in a second position relative to the drive sleeve.

Referring now to FIGS. 10-12, various stages of the driving tool 102 during the first mode of operation (i.e., during insertion of the anchor member 12 to the predetermined final depth) are illustrated. In particular, FIG. 10 illustrates the driving tool 102 holding the anchor member 12 adjacent an outer surface 300 of a target bone 302 at the orientation at which the anchor member 12 is to be inserted. The drive adapter 104 and the drive sleeve 106 in FIG. 10 are shown in the initial position. Each of the opposed slots 166 can include a first portion 166a and a third portion 166c separated by a second, intermediate portion 166b. The first and third portions 166a, 166c of each slot 166 can each extend in a direction parallel with the longitudinal axis Z, and can be circumferentially offset from one another about the longitudinal axis Z. The second portion 166b of each slot 166 can extend in a circumferential direction.

In the first slot portion 166a, the sleeve wall 142 can define a first end 251, a second end 252 opposed to and distally spaced from the first end 251, and lateral sides 261, 262 extending between the first and second ends 251, 252.

In the second slot portion 166b, the sleeve wall 142 can define a third end 253, a fourth end 254 opposed to and circumferentially spaced from the third end 253, and lateral sides 263, 264 extending between the third and fourth ends 253, 254. In the third slot portion 166c, the sleeve wall 142 can define a fifth end 255, a sixth end 256 opposed to and distally spaced from the fifth end 255, and lateral sides 265, 266 extending between the fifth and sixth ends 255, 256. One of the lateral sides 261, 262 of the sleeve wall 142 in the first portion 166a of the slots 166 can be a rotationally leading side 261, and the other can be a rotationally trailing side 262. In embodiments where the driving tool 102 is configured to insert the anchor member 12 according to the "right hand rule," the rotationally leading side 261 of the wall 142 in the first slot portion 166a is located on the left side of the slot 166 as depicted in FIGS. 10-12, and the rotationally trailing side 262 of the wall 142 in the first slot portion 166a is located on the right side of the slot 166. The pin 162 can transfer the majority, or even substantially all, of the rotational driving force from the adapter body 120 to the sleeve body 140 by driving against the rotationally leading side 261 of the sleeve wall 142 in the first slot portion 166a of each of the slots 166. It is to be appreciated that, on a fixation element 2 designed for insertion according to the right hand rule, the threads 32 of the shaft 28 of the anchor member 12 are angled such that clockwise rotation of the anchor member 12, as viewed from the central axis 4 or longitudinal axis Z at a location proximally of the proximal end 18 of the anchor member 12, causes the threads 32 to engage the bone (or whatever material in which the anchor member 12 is being inserted) in a manner driving the anchor member 12 into the bone.

In the initial position, the pin 162 can abut the first end 251 of the first slot portion 166a. As the drive adapter 104 is pushed distally and rotated about the longitudinal axis Z, the axial and rotational driving forces are applied to the fixation element 2, causing the anchor member 12 to engage and penetrate the target bone 302. The biasing member 170 can provide an axially opposed biasing force greater than the axial force necessary to penetrate the target bone 302, such that, as the anchor member 12 is inserted deeper in to the target bone 302, the drive adapter 104 remains in the initial position relative to the drive sleeve 106 as the distal end 114 of the drive sleeve 104 approaches the outer surface 300 of the target bone 302. Thus, during a first portion of the first mode of operation (i.e., until the distal end 114 of the drive sleeve 106 contacts the outer surface 300 of the target bone 302), the biasing member 170 can maintain the drive adapter 104 and the drive sleeve 106 in a translatably fixed position relative to each other along the longitudinal axis Z. It is to be appreciated that the biasing member 170 may be characterized as a "coupler" or a "coupling element."

As can be seen in FIG. 11, the drive adapter 104 and the fixation element 2 remain in the initial position until the distal end 114 of the drive sleeve 106 contacts the outer surface 300 of the target bone 302. Referring now to FIG. 12, as the driving tool 102 continues to drive the anchor member 12 into the target bone 302, abutment of the drive sleeve 106 against the outer surface 300 of the target bone 302 can impede further distal translation of the drive sleeve 106 relative to the target bone 302. However, the axial biasing force of the biasing member 170 is selected so as to be overcome by the axial driving force required for the anchor member 12 to further penetrate the target bone 302 after the distal end 114 of the drive sleeve 106 contacts the target bone 302. Thus, after the distal end 114 of the drive sleeve 106 abuts the outer surface 300 of the target bone 302, and the driving tool 102 is pressed with sufficient axial force to drive the anchor member 12 further into the target bone, (i.e., during a second portion of the first mode of operation) the drive adapter 104 and the fixation element 2 can translate longitudinally relative to the drive sleeve 106 in the distal direction. Concurrently, the pin 162 moves distally along the opposed slots 166 from the first end 151 toward the second end 252 of the first portion 166a of each of the slots 166. Thus, the pin 162 can provide the user with direct visual indication of the longitudinal position of the drive adapter (and thus an indirect visual indication of the longitudinal position of the fixation element 2) relative to the drive sleeve 106. The cylindrical outer surface 158 at the distal portion 126 of the adapter body 120 may also include markings 340, such as sequential lines, to provide the user with another visual indication of the various longitudinal position of the fixation element 2 relative to the drive sleeve 106.

The sleeve body 140 can also define a second plurality of opposed slots 193 located at least partially in the distal portion 152 of the sleeve body. The second pair of opposed slots 193 can each extend radially through the sleeve wall 142 and can provide the user with a direct visual indication of the longitudinal position of the fixation element 2 within the drive sleeve 106, even after the distal end 114 of the drive sleeve 106 contacts the bone 302. The second pair of opposed slots 193 can also provide an opening for effluent, such as blood, marrow, and/or other bone cuttings, to escape from the distal portion 152 of the sleeve body 140 and avoid clogging or impeding use of the driving tool 102.

FIG. 12 illustrates the drive adapter 104 and the fixation element 2 in the fully inserted position relative to the drive sleeve 106, at which position the anchor member 12 is fully inserted at the predetermined final depth within the target bone 302, and the driving tool 102 enters the second mode of operation, wherein each projection 36 of the anchor member 12 clears the rotationally leading surface 208 of each tab 202, as set forth more fully below. Additionally, at the fully inserted position, the pin 162 can be spaced from the first end 251 and located proximate the second end 252 of the first portion 166a of each slot 166, yet can also remain in contact with the rotationally trailing side 262 of the sleeve wall 142 within the first portion 166a of each of the slots 166. Additionally, as the drive adapter 104 and the fixation element 2 translate distally with respect to the drive sleeve 106 from the initial position to the fully inserted position, the engagement elements 30 of the fixation element 2 translate distally along the force transmission elements 200 of the driving tool 102.

The third portions 166c of the pair of opposed slots 166 can allow the user to fully retract the drive sleeve 106 relative to the drive adapter 104 for cleaning or other purposes prior to, subsequent to, or during use of the driving tool during the first and second modes of operation. For example, the user can manually retract the drive sleeve 106 relative to the adapter 104 to clean or inspect the fixation element 2 during use. The intermediate portion 124 of the adapter body can include a boss 194 defining a shoulder 196 configured to abut the proximal end 112 of the sleeve 106 in a manner limiting proximal translation of the drive sleeve 106 relative to the adapter body 120. The second portions 166b of the pair of opposed slots 166 allow the user to rotate the drive sleeve 106 relative to the adapter body 104 to transition the pin 162 from the first 166a to the second portions 166b of the slots 166. In some embodiments (not shown), the lower lateral side 263 of the second portion 166b of each of the slots 166 can be canted in the distal direction in a manner causing the pin 162 to automatically transition from the second portions 166b of the slots 166 to the first portions 166a responsive to the biasing force of the biasing member 170 if the user inadvertently leaves the adapter 104 and the sleeve 104 in relative positions such that the pin 162 is positioned in the second 166b or third 166c portions of the slots 166.

Figure 13:
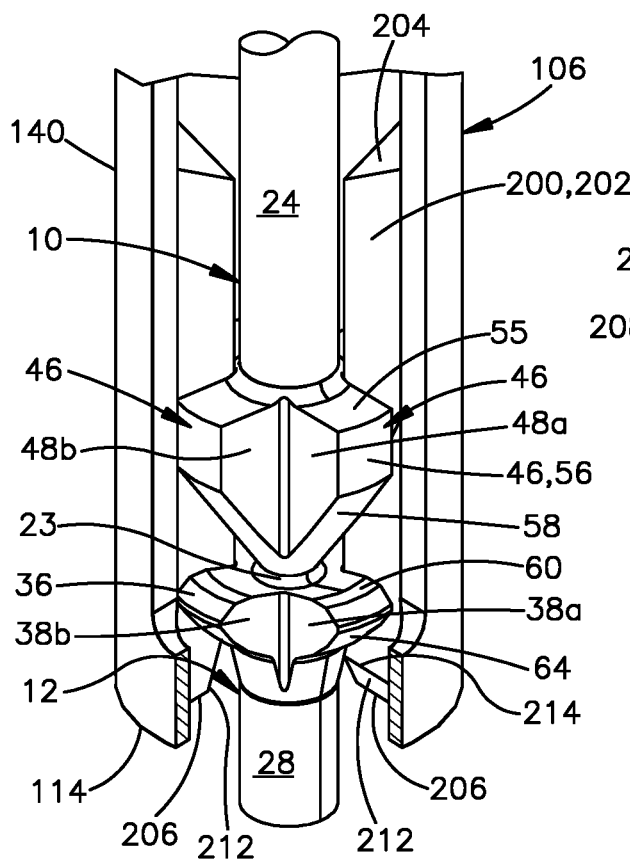
FIG. 13 is partially cutaway, perspective view of the distal end of the drive sleeve illustrated in FIGS. 7-8.

Referring now to FIG. 13, the force transmission elements 200 can include a plurality of tabs 202 extending radially inward from the inner surface 146 of the sleeve body 140 toward the longitudinal axis Z of the driver tool 102. Each of the tabs 202 can also extend substantially longitudinally from a tab proximal end 204 to a tab distal end 206. The distal ends 206 of the tabs 202 can be coincident with the distal end 114 of the drive sleeve 106. Each tab 202 can include a rotationally leading surface 208 and a rotationally trailing surface 210. The rotationally leading and trailing surfaces 208, 210 can each be substantially planar, although other geometries are within the scope of the present disclosure.

The tabs 202 can each have a longitudinal length greater than a maximum longitudinal distance between the rear segment 55 of the projections 46 of the removable member 10 and the front segment 64 of the projections 36 of the anchor member 12. Thus, when the sleeve 106 is in the initial position relative to the drive adapter 104, each tab 202 can span at least the entire length of each pair of projections 36, 46. In this manner, the tabs 202 can provide radial support to the fixation element 2 and prevent buckling at the neck 23 under the axial driving force.

Figure 14:
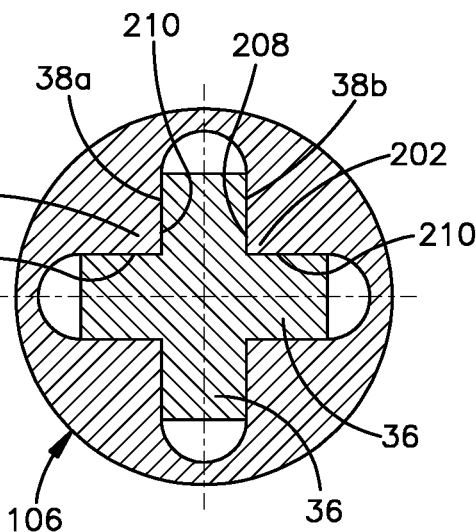
FIG. 14 is a sectional end view of a distal portion of the drive sleeve, taken along section line 14-14 of FIG. 11.

As shown in FIG. 14, the number of tabs 202 of the drive sleeve 106 can coincide with the number of associated pairs of projections 36, 46 of the fixation element 2. For example, in embodiments where the fixation element 2 includes four (4) associated pairs of projections 36, 46, the sleeve body 140 can include four tabs 202 spaced at 90° intervals about the longitudinal axis Z of the driver tool 2. Additionally, the rotationally leading and trailing surfaces 208, 210 of each tab 202 can extend at right angles (90°) relative to each other. In such embodiments, the rotationally leading surface 208 of each tab 202 can be parallel with the associated pair of lateral surfaces 38b, 48b on the rotationally trailing sides 44, 54 of the associated pairs of projection 36, 46 of the fixation element 2 when the leading surface 208 of each tab 202 abuts the associated pair of trailing lateral surfaces 38b, 48b. Additionally, the rotationally trailing surface 210 of each tab 202 can be parallel with the associated pair of lateral surfaces 38a, 48a on the rotationally leading sides 42, 52 of the associated pairs of projection 36, 46 when the trailing surface 210 of each tab 202 abuts the associated pair of leading lateral surfaces 38a, 48a. In further embodiments, the tabs 202 of the sleeve body 140 and the pairs of projections 36, 46 of the fixation element 2 can each be cooperatively sized and configured such that tabs 202 nest snuggly between the adjoining lateral surfaces 38, 48 of the associated pairs of projection 36, 46 of the fixation element 2, providing stability to the driving tool 2 and the fixation element 2 during insertion of the anchor member 12 in the target bone.

As the drive adapter 104 and the fixation element 2 move relative to the drive sleeve 106 from the initial position to the fully inserted position, the pairs of lateral surfaces 38, 48 of the engagement elements 22 of the fixation member 2 travel distally along the tabs 202 of the drive sleeve 106.

Figure 15:
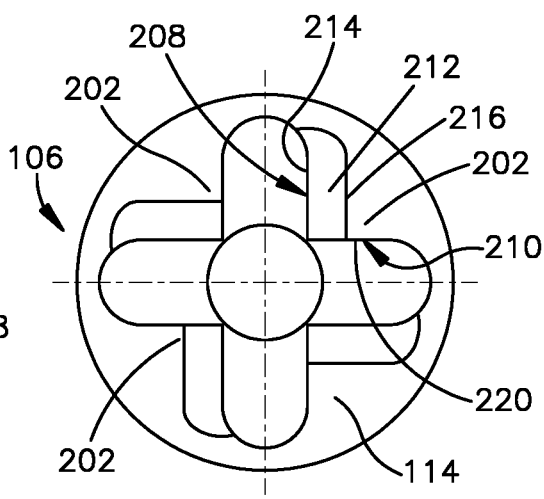
FIG. 15 is a bottom view of the distal end of the drive sleeve shown in FIG. 7.

Referring now to FIGS. 13 and 15, the distal end 206 of each tab 202 can define a ramped surface 212 inclined toward the direction of rotation. A rotationally leading edge 214 of each ramped surface 212 can be contiguous with the rotationally leading surface 208 of the associated tab 202. A rotationally trailing edge 216 of each ramped surface 212 can be contiguous with the distal end 114 of the drive sleeve 106. The ramped surface 212 of each tab 202 can be sized and oriented so as to provide a space located longitudinally between each ramped surface 212 and the distal end 114 of the drive sleeve 106. The rotationally leading edge 214 of each ramped surface 212 can be spaced from the distal end 114 of the drive sleeve 106 by a clearance distance, measured in the longitudinal direction. The clearance distance can be equivalent to or slightly greater than a seating distance of the anchor member 12, measured between the rear segment 60 of the projection 36 and the outer surface 300 of the bone 302 when the anchor member 12 is inserted at the predetermined final depth. The portion of the anchor member 12 positioned above the outer surface 300 of the bone 302 when the fixation member 12 is inserted at the predetermined final depth may be termed the "outboard portion." The ramped surfaces 212 of the tabs 202 can each be oriented at an angle θ between about 0° and about 90° relative to a direction perpendicular to the longitudinal axis Z. In other embodiments, the ramped surfaces 212 can each be oriented at an angle θ between about 35° and about 65° relative to the direction perpendicular to the longitudinal axis Z.

Figure 16:
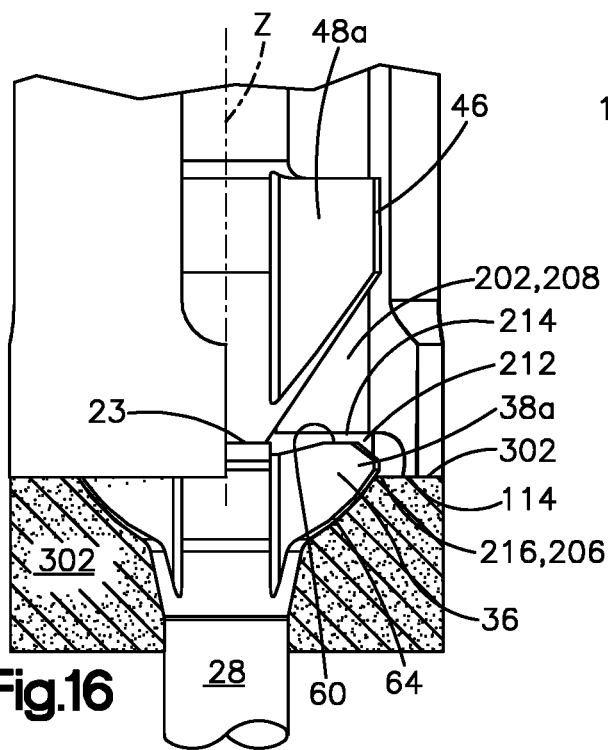
FIG. 16 is a side, partially cutaway view of the distal end of the drive sleeve, with the fixation element shown in a fully inserted position.

FIG. 16, illustrates a magnified side view of the distal end 114 of the drive sleeve 106, wherein the drive sleeve 106 is partially cut away in a manner depicting the fixation element 2 in the fully inserted position relative to the drive sleeve 106 (i.e., the anchor member 12 is inserted in the target bone 302 at the predetermined final depth). As can be seen, a portion of the projection 36 of the anchor member 12 is positioned longitudinally underneath the rotationally leading edge 214 of the ramped surface 212 at the distal end 206 of an adjacent tab 202. In this manner, once the anchor member 12 reaches the final predetermined depth (i.e., the fully inserted position), the driving tool 102 enters the second mode of operation, wherein each projection 36 of the anchor member 12 clears the rotationally leading surface 208 of each tab 202. However, the rotationally leading surfaces 208 of the tabs 202 can remain engaged with the rotationally trailing surfaces of the projections 46 of the removable member 10, imparting a majority, or even substantially all, of the rotational driving force to the projections 46 of the removable member 10. In this manner, a torque differential is imparted between the removable member 10 and the anchor member 12. The diameter $D_3$ of the neck 23 can be sized such that the torque differential sufficient to fracture the neck 23 is less than the torque differential required to further rotate the anchor member 12 after the projections of the anchor member 12 have cleared the rotationally leading surfaces 208 of the tabs 202. Thus, the insertion system 100 can be precisely designed and configured to cause the fixation element 2 to fracture at the attachment location 21 once the anchor member 12 reaches the predetermined final depth in the bone 302.

Additionally, once the neck 23 factures, the drive adapter 104 and the drive sleeve 106, with the removable member 10 of the fixation element 2 remaining coupled thereto, can continue to rotate relative to the fully inserted anchor member 12 about the longitudinal axis Z. The ramped surfaces 212 of the tabs 202 can engage the outboard portion of the projections 36 of the anchor member 12 in a manner allowing the distal ends 206 of the tabs 202 to slide up and over the outboard portions without providing enough torque to the outboard portions to further rotate the anchor member 12. In this manner, continued rotation of the drive sleeve 106 after the anchor member 12 has reached the predetermined final depth may not result in over-rotation of the anchor member 12 within the target bone 302. Thus, it can be understood that, in some embodiments, after the neck 23 fractures, the tabs 202 do not drive the anchor member 12 further into the bone 302 when the rear segments 60 of the projections 36 of the anchor member 12 are distally separated from the rotationally leading surfaces 208 of the tabs 202. Accordingly, harmful effects on the patient resulting from over-rotation of over-seating of the anchor member 12 can be prevented. Moreover, the tabs 202, their ramped surfaces 212 and distal ends 206 may be characterized as depth control features, as the clearance distance at the distal ends 206 of the tabs, and the size and orientation of the ramped surfaces 212, can effectively determine the insertion depth at which the anchor member 12 ceases to rotate and drive further into the target bone 302. Additionally, the tabs 202, their ramped surfaces 212 and distal ends 206 may be characterized as torque control features, as the maximum torque applied to the anchor member 12 can be determinative based upon the final predetermined depth at which the anchor member 12 is inserted.

Referring again to FIG. 15, the rotationally trailing surface 210 of each tab 202 can define, at the distal end 206 thereof, can define a portion 220, also termed a "reverse engagement portion," that can be flush with the distal end 114 of the drive sleeve 106. The reverse engagement portions 220 of the tabs 202 will now be discussed. As set forth above, the rotationally trailing surface 210 of each tab 202 can be parallel with the lateral surface 38a on the rotationally leading side 42 of the associated projection 36 of the anchor member 12 when the trailing surface 210 of the tab 202 abuts the leading lateral surfaces 38a. Thus, once the anchor member 12 is inserted to the predetermined final depth, the ramped surfaces 212 allow the tab distal ends 206 to slide up and over the outboard portions of the projections 36 of the anchor member, and subsequently down again into engagement with the outer surface 300 of the bone 302, once the tabs 202 rotate to the space between successive projections 36.

If the physician desires to back-out (i.e., unscrew) the anchor member 12, he or she can position the distal end 114 of the drive sleeve 106 over the outboard portion of the anchor member, such that the tabs 202 are positioned between successive outboard portions of the projections of the anchor member 12 and the distal end 114 of the drive sleeve 106 is in contact with the bone surface 254. The physician can drive the sleeve 106 in the reverse direction, wherein the reverse engagement portions 220 of the tabs 202 can engage outboard portions of the rotationally leading lateral surfaces 38a of the associated projections 36 with sufficient torque to cause the anchor member 12 to back-out from the target bone. In this manner, the insertion system 100 described herein can provide an operator, such as a physician, with finely tuned depth control in the forward (i.e., distal) and reverse (i.e., proximal) directions.

Figure 17:
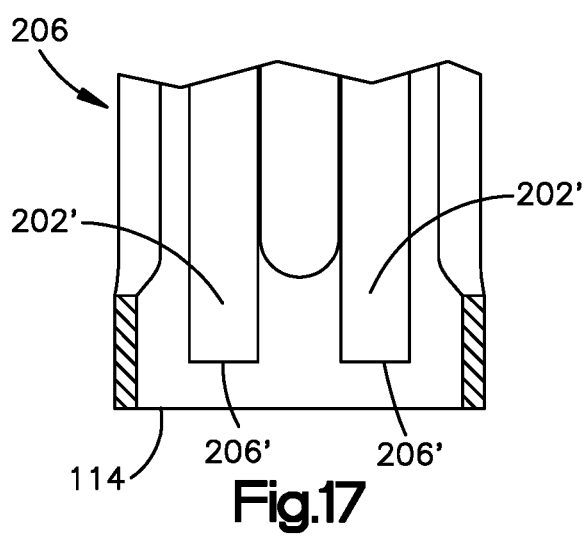
FIG. 17 is a sectional view of the distal end of the drive sleeve, taken along the longitudinal axis of the drive sleeve, according to another embodiment of the present disclosure.

Referring now to FIG. 17, a distal end 114 of the drive sleeve 106 is shown according to an additional embodiment, wherein like reference numbers refer to like components of the embodiments set forth above. In particular, in the embodiment of FIG. 17, the tabs 202' do not include ramped surfaces 212 contiguous with the distal end 114 of the drive sleeve 106. Instead, in this additional embodiment, the entire distal end 206' of each tab 202' can be located proximally of the distal end 114 of the drive sleeve 106 by the clearance distance. In such an embodiment, the tabs 202' can apply the torque differential between the anchor member 12 and the removable member 12 sufficient to fracture the neck 23 therebetween, but will not provide back-out functionality once the anchor member 12 has cleared the distal ends 206' of the tabs 202'. However, as with the embodiments illustrated above, over-rotation of the anchor member 12 within the target bone can be prevented.

Figure 18:
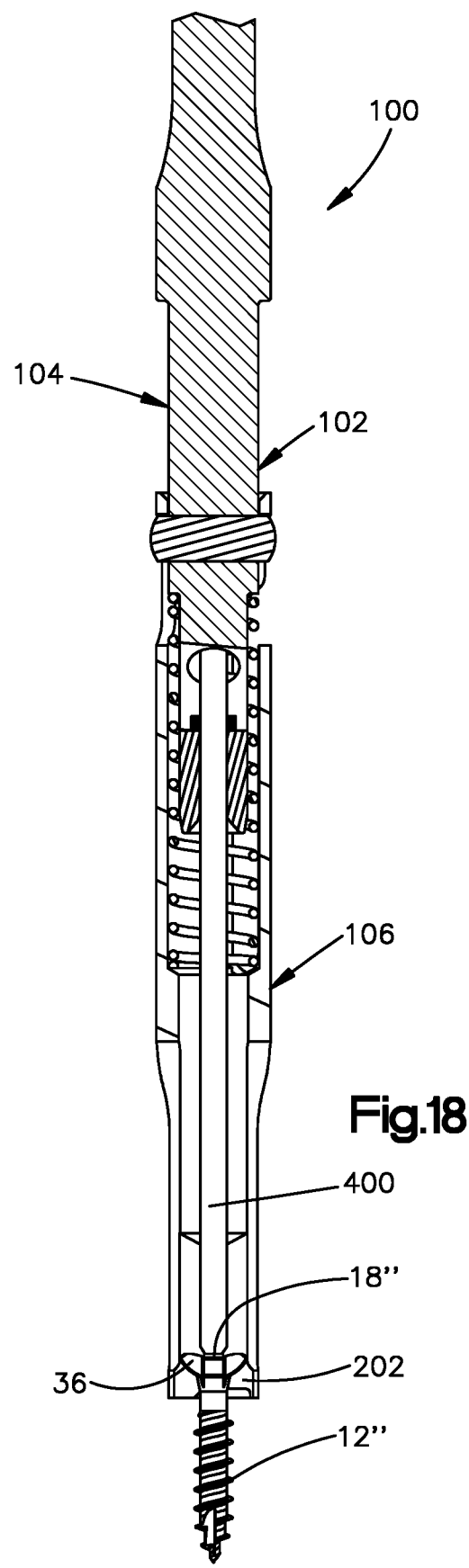
FIG. 18 is a sectional view of the driving tool, taken along the longitudinal axis of the driving tool, according to an additional embodiment of the present disclosure.

FIG. 18 illustrates a driving system 100 according to a further embodiment, wherein like reference numbers refer to like components of the embodiments set forth above. In the embodiment of FIG. 18, the anchor member 12" is not be coupled to a removable portion 10. Instead, the driving tool 102" can carry a pusher member 400 configured to abut the proximal end 18" of the anchor member 12" in a manner providing the axial driving force to the anchor member 12" during insertion. The rotational driving force can be applied to the projections 36 of the anchor member 12" by the tabs 202 in the manner set forth above.

In yet another embodiment, a kit can include a plurality of fixation elements 2, wherein each of the plurality of fixation elements 2 comprises a different configuration, size, or material. The kit can further contain a plurality of drive sleeves 106 associated with the various sizes of the fixation elements 2. The kit can be especially useful in trauma environments, for ease of use and simplicity.

It is to be appreciated that the fixation elements 2 and associated driving tools 102 disclosed herein can also be configured and utilized for affixing bone plates of various sizes and configurations to bone.

Although various embodiments have been described in detail, it should be understood that various changes, substitutions, and alterations can be made herein without departing from the spirit and scope of the disclosure as defined by the appended claims. Moreover, the scope of the present application is not intended to be limited to the particular embodiments of the process, machine, manufacture, composition of matter, methods and steps described in the specification. As one of ordinary skill in the art will readily appreciate from the present disclosure, processes, machines, manufacture, composition of matter, methods, or steps, presently existing or later to be developed that perform substantially the same function or achieve substantially the same result as the corresponding embodiments described herein can be utilized.

It will be appreciated by those skilled in the art that various modifications and alterations to the embodiments described herein can be made without departing from the broad scope of the appended claims. Some of these have been discussed above and others will be apparent to those skilled in the art.

We claim:

1. A fixation element, comprising:
    an anchor member having a proximal end and a distal end spaced from the proximal end along a central axis, the anchor member having a first plurality of engagement elements sized and configured to receive a driving torque that drives the anchor member; and
    a removable member having a proximal end and a distal end spaced from the proximal end along the central axis, the removable member adjoined with the anchor member at an interface, the removable member including a second plurality of engagement elements sized and configured to receive the driving torque, wherein the interface is configured to fracture responsive to a predetermined torque differential between the removable member and the anchor member, and
    wherein the first plurality of engagement elements comprises a first plurality of projections, the second plurality of engagement elements comprises a second plurality of projections, each of the projections of the first and second plurality of projections extends radially outward and defines a pair of opposed surfaces and a peripheral surface extending between the pair of opposed surfaces, and the opposed surfaces of each pair are substantially parallel with one another and with the central axis.

2. The fixation element of claim 1, wherein the anchor member defines a head at the proximal end thereof, the first plurality of projections are disposed on the head, the second plurality of projections are disposed on the removable member at a location adjacent the distal end of the removable member, the interface defines a radius measured from the central axis, and the radius is less than a minimum radial distance measured from the central axis to each of the opposed surfaces of the second plurality of projections.

3. The fixation element of claim 2, wherein the anchor member defines a shaft extending from the head in a distal direction.

4. The fixation element of claim 3, wherein the first plurality of projections each define a front segment that tapers inwardly and distally.

5. The fixation element of claim 4, wherein the front segments of the first plurality of projections each have respective convex arcuate profiles in respective reference planes extending along the central axis.

6. The fixation element of claim 4, wherein the anchor member further defines a tapered portion that tapers inwardly and distally from the front segments to the shaft.

7. The fixation element of claim 6, wherein the tapered portion tapers inwardly and distally at a taper angle in a range of about 5 degrees to about 25 degrees.

8. The fixation element of claim 6, wherein the first plurality of projections each define a rear segment and one or more intermediate segments extending distally between the rear segment and the front segment.

9. The fixation element of claim 8, wherein the rear segment defines the proximal most end of the respective one of the first plurality of projections.

10. The fixation element of claim 9, wherein the rear segments of the first plurality of projections are spaced proximally from the interface.

11. The fixation element of claim 3, wherein the second plurality of projections each define a front segment that tapers inwardly and distally and is contiguous with the interface.

12. The fixation element of claim 3, wherein the removable member includes a post extending in a proximal direction to the proximal end of the removable member.

13. The fixation element of claim 12, wherein the post is cylindrical.

14. The fixation element of claim 13, wherein the post defines a first diameter, the shaft defines a second diameter, and the interface defines a third diameter that is less the first and second diameters.

15. The fixation element of claim 14, wherein the first diameter is about 1.4 mm, the second diameter is about 2.0 mm, and the third diameter is about 0.8 mm.

16. The fixation element of claim 15, wherein the fixation element is constructed of a material comprising a titanium-aluminum-niobium (TAN) alloy.

17. The fixation element of claim 15, wherein the interface is configured to fracture when the predetermined torque differential is about 0.93 Newton-meters (N*m).

18. The fixation element of claim 13, wherein the removable member defines a total length of about 20 mm.

19. The fixation element of claim 1, wherein the first plurality of projections consists of four projections spaced at ninety-degree intervals about the central axis.

20. The fixation element of claim 1, wherein the second plurality of projections consists of four projections spaced at ninety-degree intervals about the central axis.

* * * * *